US006485784B1

(12) United States Patent
Leedham et al.

(10) Patent No.: US 6,485,784 B1
(45) Date of Patent: Nov. 26, 2002

(54) PRECURSORS FOR GROWTH OF HETEROMETAL-OXIDE FILMS BY MOCVD

(75) Inventors: Timothy J Leedham, Diss (GB); Peter J Wright, Malvern (GB); Anthony C Jones, Prescolt (GB); Michael J Crosbie, Pershore (GB)

(73) Assignee: Qinetiq Limited, London (GB)

( * ) Notice: Subject to any disclaimer, the term of this patent is extended or adjusted under 35 U.S.C. 154(b) by 0 days.

(21) Appl. No.: 09/720,545

(22) PCT Filed: Jun. 29, 1999

(86) PCT No.: PCT/GB99/01923

§ 371 (c)(1),
(2), (4) Date: Jan. 26, 2001

(87) PCT Pub. No.: WO00/00497

PCT Pub. Date: Jan. 6, 2000

(30) Foreign Application Priority Data

Jun. 30, 1998 (GB) .............................. 9814048

(51) Int. Cl.$^7$ ............................ C23C 16/40; C07F 3/00
(52) U.S. Cl. ............................ 427/255.31; 427/255.32; 556/28; 556/42
(58) Field of Search ...................... 427/255.32, 255.31; 556/28, 42

(56) References Cited

U.S. PATENT DOCUMENTS 5,258,204 A * 11/1993 Wernberg et al. ........... 427/108

FOREIGN PATENT DOCUMENTS

| EP | 0 807 965 A | 11/1997 |
| JP | 2001-181288 | * 7/2001 |

OTHER PUBLICATIONS

Chemical Abstracts, vol. 130, No. 20, May 1999 Columbus, Ohio, US; abstract No. 274975, Kato, K. et al.: "Formation of complex alkoxides to control layer structure in Sr–Bi–M–O (M Ta or Nb) perovskite thin films" abstract & J. Mater. Sci.: Mater. EElectron. (1998) 9(6), 457–464.

* cited by examiner

Primary Examiner—Timothy Meeks
(74) Attorney, Agent, or Firm—Nixon & Vanderhye P.C.

(57) ABSTRACT

Metalorganic precursors for deposition of strontium tantalum and strontium niobium oxides by MOCVD techniques have the formula $Sr[M(OR_1)_{6-x}L_x]_2$ wherein x is form 1 to 6; M is Ta or Nb; $R_1$ is a straight or branched chain alkyl group; and L is an alkoxide group.

40 Claims, 4 Drawing Sheets

PRECURSORS FOR GROWTH OF HETEROMETAL-OXIDE FILMS BY MOCVD

The present invention relates to novel precursors for the production of heterometal oxide films by MOCVD, in particular precursors for the growth of strontium tantalum/niobium oxide films.

The ferroelectric metal oxides (strontium bismuth tantalate ($SrBi_2Ta_2O_9$ or SBT) and strontium bismuth niobate ($SrBi_2Nb_2O_9$ or SBN) have a net electric dipole in a certain direction which can be reversed by an applied voltage. These ferroelectric materials retain a remnant polarisation (i.e. charge) even after the power has been switched off which gives them a large potential application in computer technology as capacitor layers in non-volatile ferroelectric random access memories (NVFERAM's). NVFERAM's can also be switched extremely rapidly (in hundredths of a nanosecond) and are particularly suitable for military and space applications as they are radiation hard.

Thin films of the layered perovskite strontium bismuth tantalate $SrBi_2Ta_2O_9$ (SBT), comprising ferro-electric pseudo-perovskite lattices sandwiched between bismuth oxide layers, have a large potential application as capacitor layers in non-volatile ferroelectric computer memories. In contrast to capacitors based on other ferroelectric oxides, such as $Pb(Zr,Ti)O_3$, those based on SBT show negligible polarisation fatigue, are fully compatible with conventional Pt-electrode technology, and maintain good electrical properties, even when very thin.

SBT thin films have been deposited by a variety of techniques including solgel, (Y Ito, M Ushikobo, S Yokoyama, H Matsunaga, T Atsuki, T Yonezawa and K Ogi, Int Ferroelectrics, 1997, 14, 23) metalorganic decomposition (T Mihara, H Yoshirnozi, H. Watanabe and C A Pas de Arnujo, Jpn J Appl Phys, 1995, 34, 5233; T Atsuki, N Soyama, T Yonezawaq and K Ogi, Jpn. J. Appl Phys, 1995, 34, 5096), pulsed laser ablation (P X Yang, N S Zhou, L R Zheng, H X Ln and C L Lin, J Phys. D-Appl Phys, 1997, 30, 527) and metalorganic chemical vapour deposition (MOCVD) (T Ami, K Hironaka, C Isobu, N Nagel, M Sugiyama, Y Ikeda, K Watanabe, A Machida, K Miura, and M Tanaka, Mat Res Soc Symp Proc, 1996, 415, 195; T Li, Y Zhu, S Desu C H Peng and M Nagata, Appl. Phys Lett, 1996, 68, 616). MOCVD has a number of advantages over other deposition techniques as it offers the potential for large area growth, good film uniformity and composition control, and excellent conformal step coverage at device dimension <2 μm. The MOCVD technique is also fully compatible with existing silicon CVD processes.

However for the full potential of MOCVD to be realised, it is essential that precursors with the required physical properties and decomposition characteristics are available. It is important that there is an adequate temperature window between precursor vaporisation and decomposition on the substrate, the precursors need to be compatible and not pre-react, they should decompose to form a pure film of the desired metal oxide at similar substrate temperatures. Ideally, the precursors should also be of low toxicity and be relatively stable under ambient conditions.

The MOCVD of SBT and SBN has thus far been severely restricted by a lack of suitable metalorganic precursors. Conventional precursors include $Sr(thd)_2$ (where thd=2,2,6,6-tetramethyl-3,5-heptanedionate), $Bi(C_6H_5)_3$ and $Ta(OPr^1)_4(thd)$ which are generally not compatible, having widely differing physical properties and/or decomposition characteristics (M de Keijer and G J M Dormans, MRS Bulletin, 1996, 21, 37). In an effort to alleviate this problem the Sr/Ta heterometal alkoxide $[Sr\{Ta(OPr)_6\}_2]$ has been investigated as a precursor to SBT, in combination with $Bi(OBu^1)_3$. A potential advantage of this approach is that the strontium and tantalum ratio in the precursor matches the required ratio in the deposited SBT film, however, there exists the possibility that the strontium and tantalum alkoxide species will partition during precursor evaporation and transport. Another disadvantage is that $[Sr\{Ta(OR)_5\}_2]$ precursors are relatively unsaturated making them susceptible to attack by moisture and reducing their shelf life in solution-based liquid injection MOCVD.

EP-A-0 807 965 (Matsushita Electronics Corporation) Nov. 19, 1997 describes a method of forming a Bi-layered ferroelectric thin film on a substrate, using a mixed composition of a Bi-containing organic compound and a metal polyalkoxide compound.

It is an aim of the present invention to provide new metalorganic precursors for the MOCVD of SBT and SHN which may overcome the above-mentioned drawbacks.

According to one aspect of the present invention there is provided a metalorganic precursor of the formula:

wherein x is from 1 to 6;
M is Ta or Nb; $R_1$ is a straight or branched chain alkyl group; and
L is an alkoxide group of the formula:

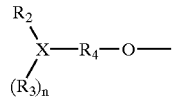

wherein n=0 or 1; X is N or O; $R_2$ and $R_3$ are the same or different and are straight or branched chain alkyl groups, and $R_4$ is a straight or branched alkyl chain, optionally substituted with an amino, alkylamino or alkoxy group.

According to a second aspect, the present invention provides a method of depositing thin films of or containing strontium metal oxides using metalorganic precursor in a MOCVD technique, wherein the strontium metal oxide precursor has the formula:

wherein x is from 1 to 6; M is Ta or Nb;
$R_1$ is a straight or branched chain alkyl group; and L is an alkoxide group of the formula:

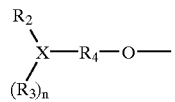

wherein n=0 or 1; X is N or O; $R_2$ and $R_3$ are the same or different and are straight or branched chain alkyl groups and $R_4$ is a straight or branched alkyl chain, optionally substituted with an amino, alkylamino or alkoxy group.

Preferably, x is 1 or 2.

The deposition, technique may comprise conventional MOCVD or, more preferably, liquid injection MOCVD. The solvent for deposition of the films by liquid injection MOCVD is preferably tetrahydrofuran.

The alkoxy group $OR_1$ is preferably an ethoxy group but compounds of the invention where $OR_1$ is, for example, an iso-propoxy or tertiarybutoxy group may also be useful. Preferred precursors of the invention have the formula:

$Sr[M(OR_1)_5L]_2$ or $Sr[M(OR_1)_4L_2]_2$ wherein M, $R_1$ and L are as defined above.

Preferably L is a dimethyl aminoalkoxide group, particularly dimethyl aminoethoxide ($OCH_2CH_2NMe_2$ or DMAE), dimethyl aminopropoxide ($OCH(CH_3)CH_2NMe_2$ or DMAP) or bis-dimethyl aminopropoxide ($OCH(CH_2NMe_2)CH_2NMe_2$ or bis-DMAP). Alternatively, L may be an alkoxy alkoxide group, particularly —$CH_2CH_2OMe$, —$OCH(CH_3)CH_2OMe$ or —$OCH(OMe)CH_2OMe$.

The above-mentioned precursors may also be used in combination with a variety of bismuth (Bi) sources to deposit strontium bismuth tantalum and strontium bismuth niobium metal oxides.

Suitable precursors for the source of bismuth include triphenyl bismuth ($Bi(C_6H_5)_3$, $Bi(thd)_3$, $Bi(OCH_2CH_2NMe_2)_3$ and $Bi(OCMe_2CH_2OMe)_3$.

The $Bi(OCMe_2CH_2OMe)_3$ precursor is particularly suitable as a co-precursor, being one of the most stable and volatile Bi alkoxide sources available.

The Bi precursors may be evaporated separately or may be combined with the $Sr[M(OR_1)_{6-x}L_x]_2$ is a single solution. In the latter case, the bismuth precursor may have the general formula $BiL_3$, wherein L is a dialkyl aminoalkoxide or alkoxy alkoxide group as hereinbefore described in relation, to the strontium metal oxide precursor. Preferably, the dialkyl aminoalkoxide or alkoxy alkoxide group of the bismuth precursor is the same as that of the strontium metal oxide precursor. The single solution may be in an organic solvent such as ether or cyclic ether (eg. THF) or a hydrocarbon, such as hexane or heptane.

The precursors of the present invention may be used in a method for depositing a strontium metal oxide ferroelectric film onto a substrate by MOCVD. A suitable substrate is, for example, Si(100). The ferroelectric films may be used, in particular, for the production of non-volatile ferroelectric random access memories.

The use of MOCVD precursor solutions containing mixtures of metal, alkoxides with nitrogen or oxygen donor functionalised ligands such as $OCH_2CH_2NMe_2$ or $OCH_2CH_2OMe$ can be readily extended to other oxide and mixed oxide systems. It has recently been shown that the dielectric constant of bulk $Ta_2O_5$ can be significantly increased by the addition of a small percentage of $TiO_2$. This offers the potential for improved performance $Ta_2O_5$—based DRAM's (dynamic random access memory). The precursor solutions described herein are likely to be appropriate for use in the MOCVD of the mixed $Ta_2O_3/TiO_2$. A suitable precursor combination is $Ta(OR)_4DMAE$ and $Ti(OR)_2(L)_2$ where R is preferably Et or alternatively may be $Pr^i$, $Pr^n$, $Bu^i$, $Bu^n$ etc., and L is DMAE, DMAP or bis-DMAP etc.

This invention will be further described, by way of example only, with reference to the accompanying drawings in which.

Figure 1:
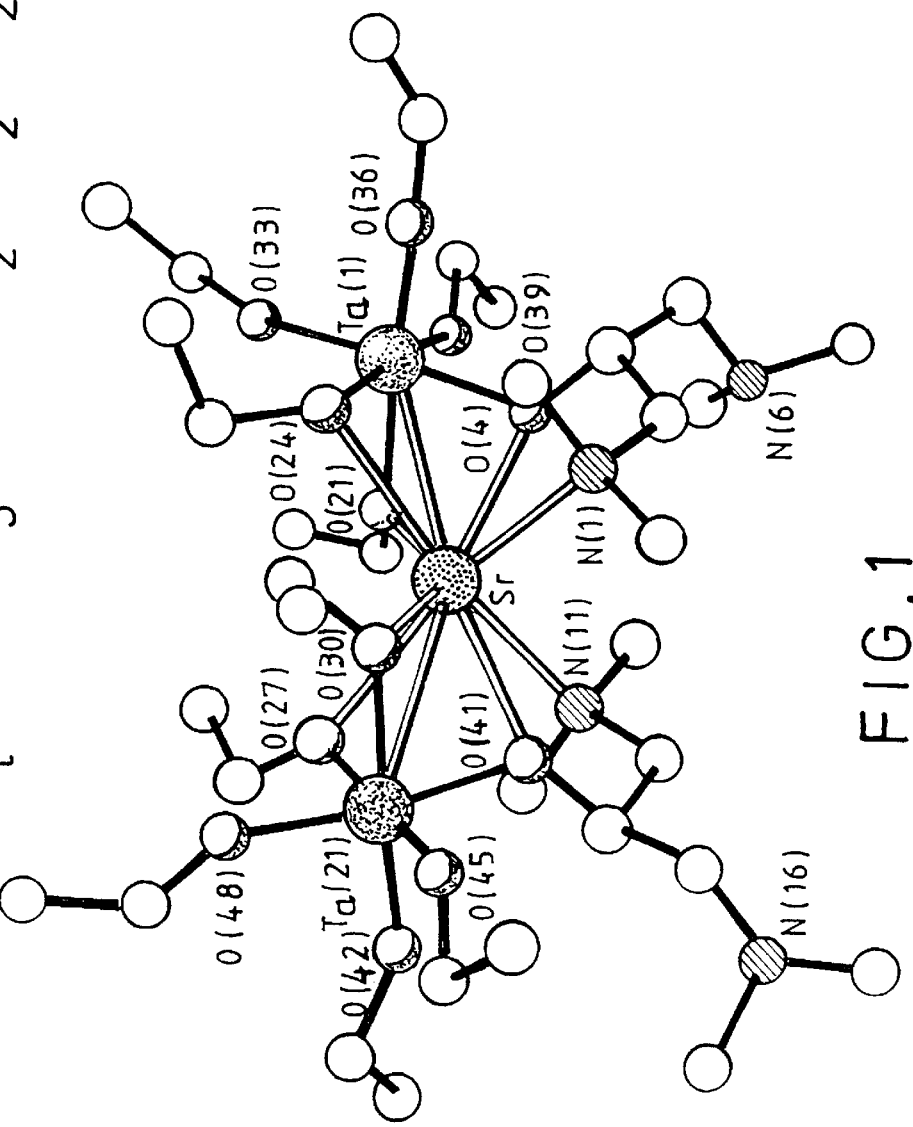
FIG. 1 illustrates the molecular structure of the novel precursor, $Sr[Ta(OEt)_5(bis-DMAP)]_2$.

The present invention examines the ways in which Sr/Ta and Sr/Nb atoms bind more strongly together in a single molecular precursor. The replacement of simple alkoxide groups by nitrogen or oxygen "donor-functionalised" alkoxides (i.e. L) increases the coordination number of highly positively charged metal centres. The crystal structure of $[Sr\{Ta(OEt)_5(bis-dmap)\}_2]$, the first structurally characterised Sr/Ta double metal alkoxide is illustrated in FIG. 1 of the accompanying drawings.

The functionalised alkoxide (such as DMAE) acts as a bridging and chelating ligand between the metal centres. This results in the precursors having appreciable volatilities and their high solubility in organic solvents favours their use in liquid injection MOCVD.

The Sr/Ta and Sr/Nb alkoxide precursors of the present invention have the two metal atoms more strongly bound together with the Sr centre being more fully saturated with a co-ordination number of 6, rendering it less susceptible to attack by moisture. In the case of bis-DMAP, it is possible that the Sr centre becomes even more fully saturated with a co-ordination number of 8.

The conventional bismuth precursors, e.g. $Bi(C_6H_5)_3$ and $Bi(thd)_3$ may be used with the heterometal alkoxide precursors of the present invention to deposit SBT or SBN. Alternatively, bismuth alkoxides having the simple alkoxide groups (ie. —OR groups) substituted with an oxygen or nitrogen donor functionalised ligand (L), eg. DMAE or DMAP, may be used as the bismuth precursor. Preferably, the bismuth precursor $Bi(OCMe_2CH_2OMe)_3$ is used as the co-precursor, being one of the most stable and volatile Bi alkoxide sources available. The use of a bismuth precursor containing such alkoxide groups may enable Bi precursors to be used which have the same donor functionalised ligand as the strontium metal oxide precursor, to enable a single precursor solution to be used in the production of strontium bismuth tantalate or strontium bismuth niobate films, thereby greatly simplifying the MOCVD process and apparatus.

The invention will also be further described by means of the following Example.

EXAMPLE

Precursor Synthesis and Characterisations (I) $Sr[Ta(OEt)_5(dmae)]_2$

A sample of $[Sr\{Ta(OEt)_6\}_2]$ (16.9 g, 17 mmol) was dissolved in n-hexane (500 ml) and bis-dmaeH (3.1 g, 34 mmol) was added with stirring. The mixture was boiled under reflux for 3 hours and was then allowed to cool. The n-hexane solvent was removed in vacuo to leave a pale yellow oil, which was purified by vacuum distillation at 90–100° C. (0.2 mm Hg) to yield the product as a colourless liquid (yield 72%).

IR (nujol mull, NaCl plates): 3350 s (broad), 2890 s (broad), 1645 m (broad), 1435 w. 1305 m, 1265 s, 1120–1070 s (v broad), 1000 m, 905 s, 825 m.

$^1$H NMR ($C_6D_6$):ä (ppm) 1.64 (t, $CH_3$, 30H), 2.63 (m, N—$CH_3$, N—$CH_2$16H), 4.71 (m, $OCH_2CH_3$, $OCH_2CH2N$, 24H).

(II) $Sr[Ta(OEt)_5(bis-dmap)]_2$

A sample of $[Sr\{Ta(OEt)_6\}]$ (16.9 g, 17 mmol) was dissolved in n-hexane (500 ml) and bis-dmapH (5 g, 34 mmol) was added, with stirring. The mixture was boiled under reflux for 3 hours and after cooling, the solvent was removed in vacuo. The resulting pale yellow oil was vacuum distilled at 185–190° C. (0.2 mm Hg) to yield a colourless liquid which solidified on standing to a white waxy solid (Yield 60%). Recrystallisation from n-hexane and storing at −20° C. for 2 weeks gave the product as colourless crystals.

IR (Nujol mull, NaCl plates): 3400 s (broad) 2900 s (broad), 1600 w (broad), 1440 s, 1410 w, 1380 s, 1320 m, 1150–1050 s (v broad), 1000 m, 910 s, 835 m, 820 m.

$^1$H NMR (C$_6$D$_6$): äx (ppm) 1.29 (t, CH$_3$, 30H), 2.18 (m, N—CH$_3$, N-CH$_2$, 32H), 4,51 (m, OCH$_2$CH$_3$, OCH$_{2\,bis\text{-}dmap}$. 22H)

Microanalysis: Calculated For C$_{34}$H$_{84}$N$_4$O$_{12}$Ta$_2$Sr: C, 34.3, H, 7.1; N, 4.7; Found C, 34.1, H, 7.1, N, 4.8.

(III) MOCVD of Strontium tantalum oxide thin films

This films of SrTa$_2$O$_6$ were deposited by liquid injection MOCVD using 0.1 molar solutions of [Sr{Ta(OEt)$_5$(dmae)}$_2$] or [Sr{Ta(OEt)$_5$(bis-dmap)}$_2$] in tetrahydrofuran solvent. The films were deposited over a range of substrate temperatures from 250–550° C. on to Si(100) single crystal substrates using an MOCVD reactor. Table 1 below illustrates the growth conditions used to deposit the strontium tantalate for the two precursors:

TABLE 1

Growth conditions used to deposit strontium tantalate from Sr{Ta(OEt)$_5$(dmae)}$_2$] and [Sr{Ta(OEt)$_5$(bis-dmap)}$_2$]

| Run number | Precursor solution injection rate [cm$^3$hr$^{-1}$] | Ar flow [cm$^3$min$^{-1}$] | O$_2$ flow [cm$^3$min$^{-1}$] | Substrate temperature [° C.] | Layer thickness$^{(a)}$ [µm] |
|---|---|---|---|---|---|
| (a) [Sr{Ta(OEt)$_5$(dmae)}$_2$] | | | | | |
| 512 | 2 | 4000 | 1000 | 400 | 0.19 |
| 513 | 2 | 4000 | 1000 | 300 | 0.37 |
| 517 | 4 | 4000 | 1000 | 350 | 0.40 |
| 520 | 2 | 5000 | 0 | 350 | 0.15 |
| 521 | 2 | 3000 | 2000 | 350 | 0.20 |
| (b) [Sr{Ta(OEt)$_5$(bis-dmap)}$_2$] | | | | | |
| 523 | 2 | 4000 | 1000 | 400 | 0.20 |
| 525 | 4 | 4000 | 1000 | 500 | 0.25 |
| 527 | 2 | 5000 | 0 | 350 | 0.17 |
| 528 | 2 | 3000 | 2000 | 350 | 0.36 |
| 530 | 2 | 4000 | 1000 | 450 | 0.51 |

$^{(a)}$Approx. values assuming layer density = density of Ta$_2$O$_5$(8.2 g cm$^{-3}$)
Reactor pressure = 760 Torr
Evaporator temperature = 200° C.
Substrates Si(100)

Figure 2:
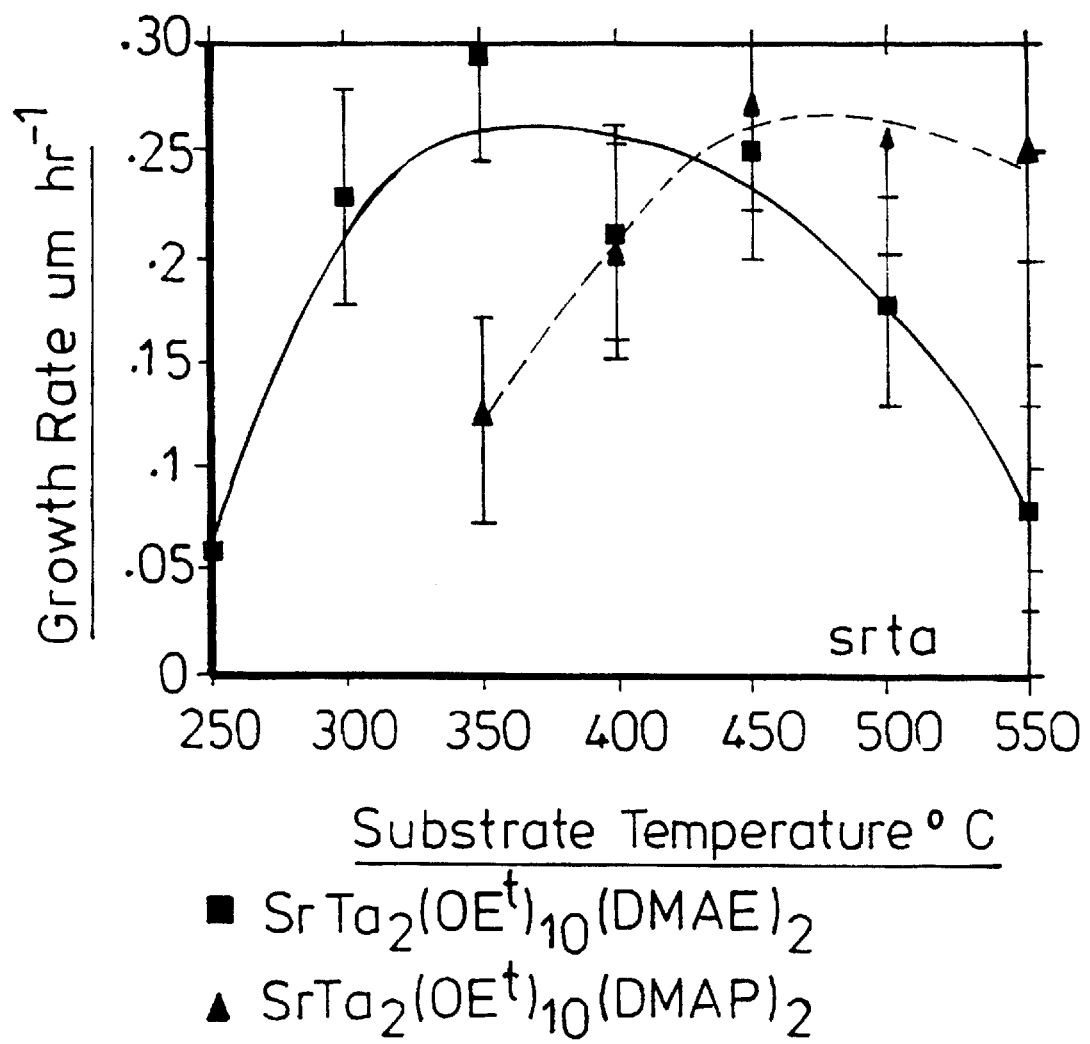
FIG. 2 is a plot of growth grates against substrate temperature achieved by MOCVD using two strontium tantalum precursors of the present invention.

FIG. 2 of the accompanying drawings illustrates the dependence of growth rate of the films on substrate temperature.

Analysis of the films prepared using the precursor [Sr{Ta(OEt)$_5$(dmae)}$_2$] by Auger electron spectroscopy (AES) showed that the films had the approximate composition SrTa$_2$O$_6$, as shown in Table 2 below:

TABLE 2

AES data (composition in atom %) for strontium tantalum oxide films grown from [Sr{Ta(OEt)$_5$(dmae)}$_2$]

| Run Number | Sr | Ta | O | C | Ta/Sr Ratio |
|---|---|---|---|---|---|
| 512 | 3.5 | 26.1 | 68.1 | 2.2 | 7.4 |
| 513 | 5.4 | 27.5 | 63.7 | 3.5 | 5.1 |
| 517 | 9.2 | 19.1 | 65.7 | 6.1 | 2.1 |
| 520 | 15.3 | 13.5 | 64.5 | 6.8 | 0.9 |
| 521 | 11.3 | 19.3 | 65.3 | 4.2 | 1.7 |

Figure 3:
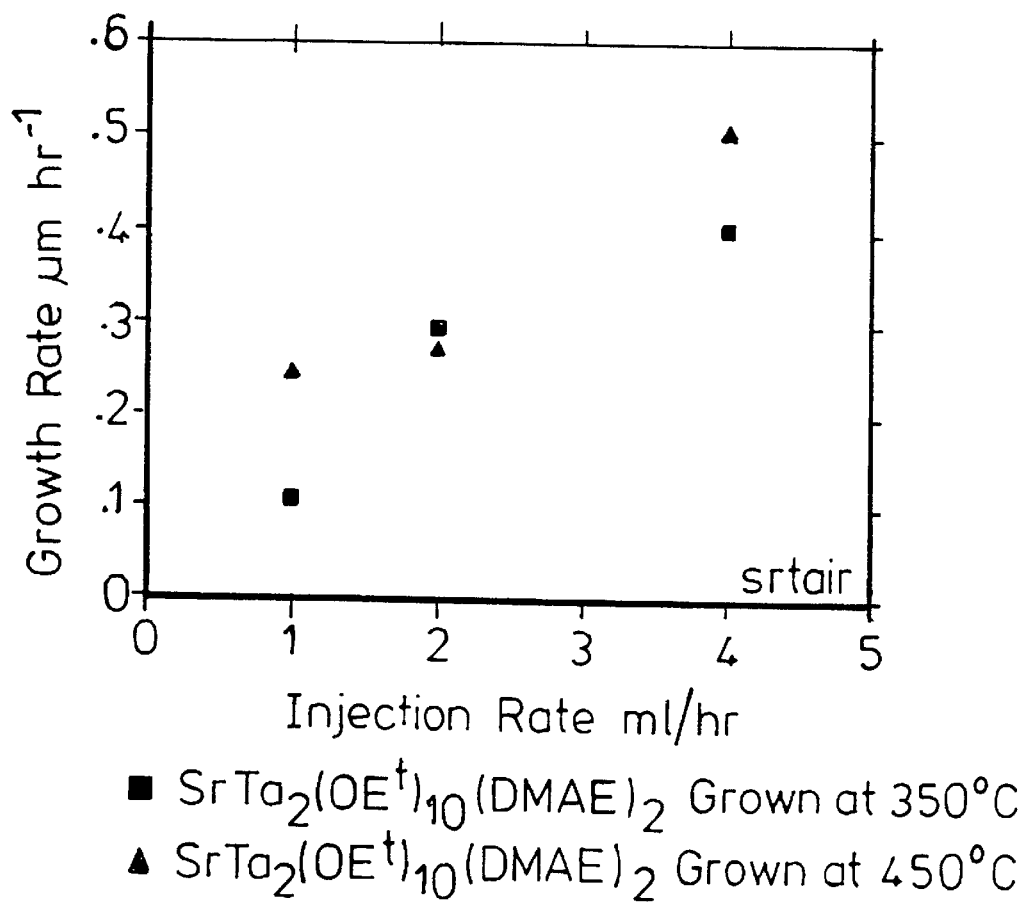
FIG. 3 is a plot of growth rates against injection rate achieved by MOCVD using two strontium tantalum precursors of the present invention.
Figure 4:
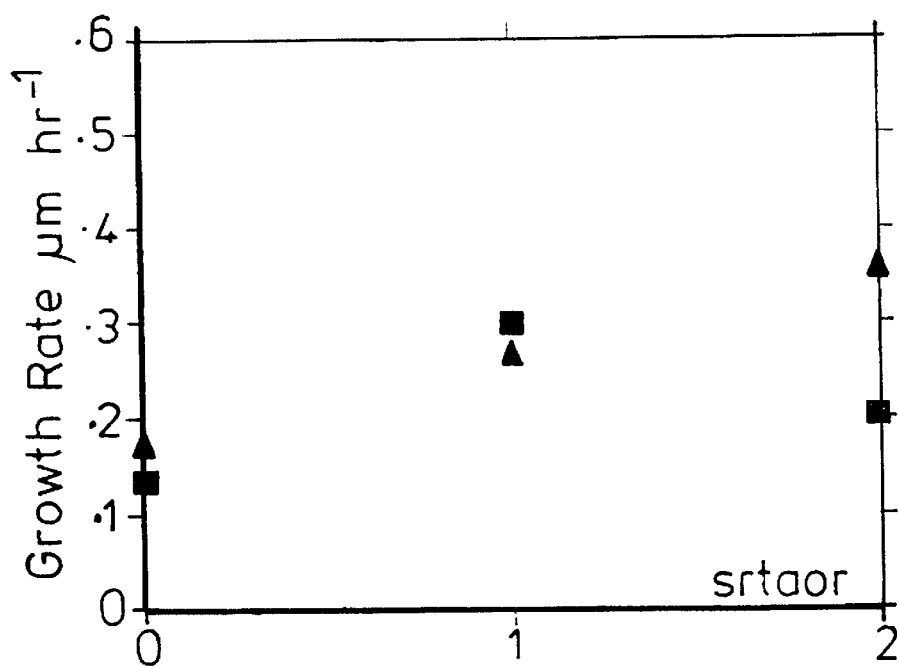
FIG. 4 is a plot of growth rates against oxygen flow achieved by MOCVD using two strontium tantalum precursors of the present invention.

The double alkoxide compounds of the present invention may be used for the growth of strontium tantalate and strontium niobate on a simple liquid injection MOCVD reactor. The reactor has two inlet lines of vaporisation and transport of the Sr/Ta, Sr/Nb and Bi(OR)$_3$ precursors, as well as an inlet for an oxidant, such as oxygen gas. FIG. 3 of the accompanying drawings illustrates the growth rate of a film of strontium tantalate against the injection rate of MOCVD using the strontium precursors SrTa$_2$(OEt)$_{10}$(DMAE)$_2$ and SrTa$_2$(OEt)$_{10}$(DMAP)$_2$. FIG. 4 shows the growth rate of the strontium tantalate against oxygen flow using the same precursors.

What is claimed is:

1. A metalorganic precursor of the formula

wherein x is from 1 to 6;
   M is Ta or Nb;
   R$_1$ is a straight or branched chain alkyl group; and
   L is an alkoxide group of the formula:

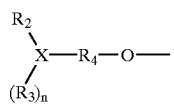

wherein n is 0 or 1
   X is N or O
   R$_2$ and R$_3$ are the same or different and are straight or branched chain alkyl groups; and
   R$_4$ is a straight or branched alkyl chain, optionally substituted with an amino, alkylamino or alkoxy group.

2. A metalorganic precursor as claimed in claim 1, wherein x is 1 or 2.

3. A metalorganic precursor as claimed in claim 1, wherein the alkoxy group OR$_1$ is an ethoxy group.

4. A metalorganic precursor as claimed in claim 1, wherein the alkoxy group OR$_1$ is an iso-propoxy group.

5. A metalorganic precursor as claimed in claim 1 wherein the alkoxy group OR$_1$ is a tertiary butoxy group.

6. A metalorganic precursor as claimed in claim 1 having the formula:

7. A metalorganic precursor as claimed in claim 1 to 5 having the formula:

8. A metalorganic precursor as claimed in claim 1, wherein L is a dimethylaminoalkoxide group.

9. A metalorganic precursor as claimed in claim 8, wherein L is dimethylaminoethoxide.

10. A metalorganic precursor as claimed in claim 8, wherein L is dimethylaminopropoxide.

11. A metalorganic precursor as claimed in claim 8, wherein L is bis-dimethylaminopropoxide.

12. A metalorganic precursor as claimed in claim 1, wherein L is an alkoxyalkoxide group.

13. A metalorganic precursor as claimed in claim 12, wherein L is —OCH$_2$CH$_2$OCH$_3$—.

14. A metalorganic precursor as claimed in claim 12, wherein L is —OCH(CH$_2$)CH$_2$OCH$_3$—.

15. A metalorganic precursor as claimed in claim 12, wherein L is —OCH(OCH$_2$)CH$_2$OCH$_3$—.

16. The metalorganic precursor as claimed in claim 1 wherein the precursor is Sr{Ta(OEt)$_5$(bis-dmap)$_2$, and bis-dmap is bis-dimethylaminopropoxide.

17. The metalorganic precursor as claimed in claim 1, wherein the precursor is S[Ta(OEt)$_5$(dmae)]$_2$, and dmae is dimethylaminoethoxide.

18. A method of depositing thin films of or containing strontium metal oxides using metalorganic precursors in an MOCVD (metalorganic chemical vapour deposition) technique, wherein the strontium metal oxide precursor has the formula

wherein x is from 1 to 6;

M is Ta or Nb;

R$_1$ is a straight or branched chain alkyl group; and

L is an alkoxide group of the formula:

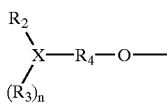

wherein n is 0 or 1

X is N or O

R$_2$ and R$_3$ are the same or different and are straight or branched chain alkyl groups; and R$_4$ is a straight or branched alkyl chain, optionally substituted with an amino, alkylamino or alkoxy group.

19. A method as claimed in claim 18, wherein x is 1 or 2.

20. A method as claimed in claim 18, wherein the alkoxy group OR$_1$ is an ethoxy group.

21. A method as claimed in claim 18 wherein the alkoxy group OR$_1$ is an isopropoxy group.

22. A method as claimed in claim 18, wherein the alkoxy group OR$_1$ is a tertiary butoxy group.

23. A method as claimed in claim 18, wherein the strontium metal oxide precursor has the formula:

24. A method as claimed in claim 18, wherein the strontium metal oxide precursor has the formula:

25. A method as claimed in claim 18, wherein L is a dimethylaminoalkoxide group.

26. A method as claimed in claim 25, wherein L is dimethylaminoethoxide.

27. A method as claimed in claim 25, wherein L is dimethylaminopropoxide.

28. A method as claimed in claim 25, wherein L is bis-dimethylaminopropoxide.

29. A method as claimed in claim 18, wherein L is an alkoxyalkoxide group.

30. A method as claimed in claim 29, wherein L is —OCH$_2$CH$_2$OCH$_3$.

31. A method as claimed in claim 29, wherein L is —OCH(CH$_3$)CH$_2$OCH$_3$.

32. A method as claimed in claim 29, wherein L is —OCH(OCH$_3$)CH$_2$OCH$_3$.

33. A method as claimed in claim 18, wherein the metalorganic precursor is Sr[Ta(OEt)$_5$(bis-dmap), wherein bis-dmap is bis-dimethylaminopropoxide.

34. A method as claimed in claim 18, wherein the metalorganic precursor is Sr[Ta(OEt)$_5$(dmae)]$_2$, wherein dmae is dimethylaminoethoxide.

35. A method as claimed in claim 18, for depositing strontium bismuth tantalum metal oxides or strontium bismuth niobium metal oxides by including a bismuth metalorganic precursor.

36. A method as claimed in claim 35, wherein the bismuth precursor is selected from the group consisting of Bi(C$_6$H$_5$)$_3$, Bi(thd)$_3$ (where "thd" is 2,2,6,6-tetramethyl-3,5-heptanedionate), Bi(OCH$_2$CH$_2$NMe$_2$)$_3$ and Bi(OCHMe$_2$CH$_2$OMe)$_3$.

37. A method as claimed in claim 35, wherein the bismuth and strontium precursors are evaporated separately.

38. A method as claimed in claim 35, wherein the bismuth and strontium precursors are combined in a single solution for MOCVD.

39. A method as claimed in claim 38, wherein the bismuth precursor has the same ligand L as the strontium precursor.

40. A method as claimed in claim 38, wherein the precursor solution is an organic solvent selected from ethers, cyclic ethers and hydrocarbons.

* * * * *